United States Patent [19]
Görög née Privitzer et al.

[11] Patent Number: 4,675,431
[45] Date of Patent: Jun. 23, 1987

[54] PHOSPHORIC ACID MONESTER SALTS

[75] Inventors: Katalin Görög née Privitzer; László Bodnár; Erzsébet Dudar; Mária Kocsis née Bági; Sándor Gaál; Márta Tasnádi; Eva Egyházi née Csizmadia; Valéria M. Varga; István Kajati, all of Budapest; Gvörgy Kis, Hatvan; János Molnár; Bertalan Tóth, both of Budapest; Ilona Cserháti née Botka, Balassagvarmat; Tibor Kaptás, Eger; Sándor Csete, Miskolc, all of Hungary

[73] Assignee: Borsodi Vegyi Kombinát, Hungary

[21] Appl. No.: 888,267

[22] Filed: Jul. 18, 1986

Related U.S. Application Data

[63] Continuation of Ser. No. 781,306, Sep. 27, 1985, abandoned, which is a continuation of Ser. No. 541,109, Oct. 12, 1983, abandoned, which is a continuation of Ser. No. 296,560, Aug. 26, 1981, abandoned.

[30] Foreign Application Priority Data

Aug. 27, 1980 [HU] Hungary ............................ 2119-80

[51] Int. Cl.$^4$ .............................................. C07F 9/141
[52] U.S. Cl. ..................................................... 558/218
[58] Field of Search ......................................... 558/218

[56] References Cited
U.S. PATENT DOCUMENTS 2,824,113  2/1958  Zech .................................... 558/133
3,354,166  11/1967  Garner ................................ 558/131

Primary Examiner—Anton H. Sutto
Attorney, Agent, or Firm—Toren, McGeady & Associates

[57] ABSTRACT

The invention relates to new compounds of the general formula I

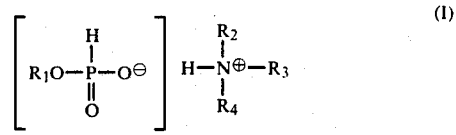

wherein
  $R_1$ is a straight or branched chained alkyl having 1 to 13 carbon atoms, optionally substituted with halogen, alkoxyalkyl containing 1 to 5 carbon atoms in the alkoxy and 1 to 4 carbon atoms in the alkyl moiety or phenyl;
  $R_2$ is alkyl having 6 to 20 carbon atoms; alkoxyalkyl, phenoxyalkyl, furfuryl, cyclopropyl-alkyl, cyclopentyl, cycloheptyl, thiazolyl, triazolyl, thiazolinyl, pyridinyl, picolyl, benzimidazolyl, piperonyl, pirimidinyl, chlorobenzothiazolyl, benzyl, phenyl substituted with chloro and/or amino, or amino and alkyl, or amino and nitro groups, alkenyl, alkinyl, aminoalkyl, dialkylamino-alkyl, alkylaminoalkyl, alkylphosphonateammoniumalkyl, 3,5-dichlorophenyl-hidantoinyl, or thiadiazolyl optionally substituted with alkyl;
  $R_3$ is hydrogen, phenyl, benzyl, alkenyl, alkyl, hydroxy, alkoxy or alkoxyalkyl; or
  $R_2$ and $R_3$ together stand for a 3,5-dichlorophenyl-hidantoinyl group;
  $R_4$ is hydrogen or alkyl optionally substituted with hydroxyl.

The new phosphoric acid monoester salts of the general formula I show fungicidal activity. The fungicidal compositions containing said compounds as active ingredients are also within the scope of the invention. According to a further aspect of the invention there is provided a process for the preparation of the new compounds.

1 Claim, No Drawings

PHOSPHORIC ACID MONESTER SALTS

This is a continuation of application Ser. No. 781,306, filed Sept. 27, 1985, which, in turn, is a continuation of application Ser. No. 541,109, filed Oct. 12, 1983, which, in turn is a continuation of application Ser. No. 296,560, filed Aug. 26, 1981, all now abandoned.

BACKGROUND OF THE INVENTION

1. Field of the Invention

The invention relates to new phosphoric acid monoester salts, a process for their preparation and fungicidal compositions containing said compounds as active ingredient.

2. Description of the Prior Art

Compounds having such fungicidal properties are reported in the following publications: Journal of Gen. Chem. USSR, 42, 1924 (1972); Chemical Abstracts 11074e, 1966; Houben-Weyl: Org. Chem. XII/2; Chem. Ber. 90, 811; Published Hungarian Patent Application Nos. PE-940, PE-936 and PI-670.

In the published Hungarian Patent Application No. PE-940, fungicially active compounds of the general formula A are disclosed.

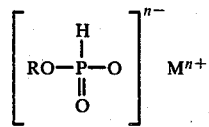

In the general formula A

R stands for a straight or branched chained alkyl group having 1 to 18, preferably 1 to 8 carbon atoms, optionally substituted with halogen; alkenyl or alkinyl having 1 to 8, preferably 1 to 5 carbon atoms; alkoxyalkyl containing 1 to 5 carbon atoms in the alkoxy moiety and 1 to 4 carbon atoms in the alkyl moiety; cycloalkyl having 3 to 6 carbon atoms; phenyl, phenyl substituted with alkyl having 1 to 4 carbon atoms or tetrahydrofurfuryl;

M is hydrogen, an ammonium cation, optionally substituted with 1 to 4 alkyl having 1 to 5 carbon atoms, hydroxyalkyl having 1 to 5 carbon atoms or phenyl; an alkali metal cation, preferably sodium or potassium ion; an alkali earth metal cation, preferably magnesium, barium or calcium ion or a multivalent metal cation, preferably zinc, manganese, cupro, cupri, iron, nickel or aluminum ion; and n represents a number equivalent to the valence of M.

SUMMARY OF THE INVENTION

We have surprisingly found that the fungicidal activity of the new compounds of the general formula I hereinbelow, according to the invention, surpasses the activity of the commercially available known compounds of the general formula A.

More particularly, the new phosphoric acid monoester salts of the present invention have the general formula I

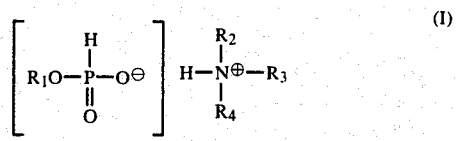

wherein $R_1$ is a straight or branched chained alkyl group having 1 to 13 carbon atoms, optionally substituted with halogen; an alkoxyalkyl group containing 1 to 4 carbon atoms in the alkyl moiety and 1 to 5 carbon atoms in the alkoxy moiety or a phenyl group;

$R_2$ is alkyl having 6 to 20 carbon atoms; alkoxyalkyl, phenoxyalkyl, furfuryl, cyclopropyl-alkyl, cyclopentyl, cycloheptyl, thiazolyl, triazolyl, thiazolinyl, pyridinyl, picolyl, benzimidazolyl, piperonyl, pirimidinyl, chlorobenzothiazolyl, benzyl, phenyl substituted with chloro and/or amino, or amino and alkyl, or amino and nitro groups, alkenyl, alkinyl, aminoalkyl, dialkylamino-alkyl, alkylaminoalkyl, alkylphosphonateammoniumalkyl, 3,5-dichlorophenylhidantoinyl or thiadiazolil optionally substituted with alkyl;

$R_3$ is hydrogen, phenyl, benzyl, alkenyl, alkyl, hydroxy, alkoxy or alkoxyalkyl; or $R_2$ and $R_3$ together stand for a 3,5-dichlorophenyl-hidantoinyl group;

$R_4$ is hydrogen or alkyl optionally substituted with hydroxyl.

Though structurally closely related compounds are known in the art and their fungicidal activity has also been reported, compounds of the general formula I, wherein $R_1$, $R_2$, $R_3$ and $R_4$ are as hereinabove described, are new.

In the definition of $R_2$ the phenoxyalkyl groups preferably contain 1 to 5 carbon atoms in the alkyl moiety, the alkenyl and alkinyl groups preferably have 2 to 5 carbon atoms, the aminoalkyl groups preferably have 1 to 10 carbon atoms in the alkyl moiety, in the alkylamino and dialkylamino groups the alkyl moieties preferably contain 1 to 6, more preferably 1 to 4 carbon atoms, and the alkyl substituents of the phenyl and thiadiazolyl groups preferably contain 1 to 6, more preferably 1 to 4 carbon atoms.

In the definition of $R_3$ the preferred alkyl substituents contain 1 to 13, more preferably 1 to 4 carbon atoms, the alkenyl groups preferably have 2 to 5, the alkoxy groups 1 to 4 carbon atoms, and the alkoxyalkyl groups preferably have 1 to 4 carbon atoms both in the alkoxy and in the alkyl moieties.

In the definition of $R_4$ the alkyl groups preferably have 1 to 13, more preferably 1 to 8, most preferably 1 to 6 carbon atoms.

DESCRIPTION OF THE PREFERRED EMBODIMENT

The compounds of the general formula I can be prepared by methods known in the art. Of these methods the followings should be particularly mentioned:

(a) a compound of the general formula II

wherein $R_1$ is an hereinabove defined, is reacted with a compound of the general formula III

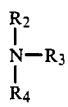

wherein $R_2$, $R_3$ and $R_4$ are as defined hereinabove, or with a hydrochloride or hydrobromide thereof;

(b) a compound of the general formula IV

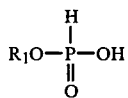

wherein $R_1$ is as hereinabove mentioned, is reacted with a compound of the general formula III, wherein $R_2$, $R_3$ and $R_4$ have the same meaning as defined above; or (c) a compound of the general formula V

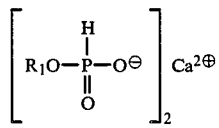

$R_1$ is as defined above, is reacted with a compound of the general formula VI $$\left[ \begin{array}{c} R_2 \\ | \\ N-R_3 \\ | \\ R_4 \end{array} \right] \cdot H_2SO_4 \quad (VI)$$

wherein $R_2$, $R_3$ and $R_4$ have the same meaning as defined above.

The process variant (a) is generally performed in an aqueous or organic reaction medium or in a mixture of water and a water-miscible organic solvent. The reaction temperature can be varied in a wide range, depending on the reactants used, but preferably is between 0° C. and 150° C., more preferably 20° C. and 110° C.

The process variant (b) preferably is carried out in an organic solvent. As an organic solvent for example benzene, toluene, xylene, chloroform, trichloroethylene can be employed. The reaction temperature can be varied in a wide range depending on the reactants used, but preferably is between 0° C. and 120° C.

The process variant (c) preferably is accomplished in an aqueous medium. The reaction temperature can be varied in a wide range, but preferably is between 0° C. and 100° C., more preferably 5° C. and 35° C.

Preferred representatives of the phosphoric acid monoester salts of the general formula I are listed in the following Table I. The Table also contains the method used for the preparation of these compounds and their physical constants.

TABLE I

| Compound No. | Process variant | Yield (%) | Melting point $n_D$ | P (%) calculated | P (%) found | N (%) calculated | N (%) found |
|---|---|---|---|---|---|---|---|
| (1) 3-isononyloxypropyl-ammoniummethyl phosphonate | a | 94.8 | $n_D^{29} = 1,4482$ | 10.42 | 10.30 | 4.71 | 4.57 |
| (2) 3-ethoxypropyl-ammoniummethyl phosphonate | a | 98.9 | $n_D^{27} = 1,4427$ | 15.56 | 15.37 | 7.03 | 6.94 |
| (3) 3-methoxypropyl-ammoniummethyl phosphonate | a | 99.9 | $n_D^{30} = 1,4449$ | 16.73 | 16.45 | 7.56 | 7.14 |
| (4) 3-butyloxypropyl-ammoniummethyl phosphonate | a | 99.4 | $n_D^{30} = 1,4420$ | 13.64 | 13.63 | 6.16 | 6.06 |
| (5) 3-ethoxypropyl-ammoniumethyl phosphonate | a | 99.9 | $n_D^{22} = 1,4445$ | 14.53 | 14.05 | 6.56 | 6.69 |
| (6) 3-methoxypropyl-ammoniumethyl phosphonate | a | 94.3 | $n_D^{30} = 1,4440$ | 15.56 | 15.48 | 7.03 | 7.17 |
| (7) 3-isononyloxypropyl-ammonium-ethyl phosphonate | a | 97.9 | $n_D^{30} = 1,4405$ | 9.95 | 9.73 | 4.49 | 4.28 |
| (8) 3-butyloxypropyl-ammoniumethyl phosphonate | a | 95.7 | $n_D^{30} = 1,4438$ | 12.84 | 12.05 | 5.80 | 5.27 |
| (9) furfuryl-ammoniummethyl phosphonate | a | 90.5 | 112–115° C. | 16.04 | 15.97 | 7.25 | 7.14 |
| (10) cyclopentyl-ammoniummethyl phosphonate | a | 99 | $n_D^{30} = 1,4463$ | 17.10 | 16.93 | 7.73 | 7.35 |
| (11) 1-methyl-2-phenoxyethyl-ammoniummethyl phosphonate | a | 81.9 | 95–96° C. | 11.86 | 11.27 | 5.36 | 5.29 |
| (12) diallyl-ammonium-ethyl phosphonate | a | 93.4 | $n_D^{30} = 1,4562$ | 14.95 | 15.02 | 6.75 | 6.05 |
| (13) allyl-ammonium-ethyl phosphonate | a | 73,0 | $n_D^{25} = 1,4517$ | 18,54 | 18,40 | 8,37 | 8,52 |
| (14) 1-propinyl-3-dimethyl-ammonium-ethyl phospho- | a | 60,5 | $n_D^{30} = 1,4481$ | | | | |

TABLE I-continued

| Compound No. | Process variant | Yield (%) | Melting point $n_D$ | P (%) calculated | P (%) found | N (%) calculated | N (%) found |
|---|---|---|---|---|---|---|---|
| (15) methyldiallyl-ammoniumethyl phosphonate | a | 66,4 | $n_D^{30}$ = 1,4462 | | | | |
| (16) thiazolyl-2-ammoniumethyl phosphonate | a | 95,1 | $n_D^{25}$ = 1,5068 | 14,76 | 14,57 | 13,32 | 13,20 |
| (17) pryidinyl-2-ammoniumethyl phosphonate | a | 95,5 | $n_D^{25}$ = 1,5092 | 15,18 | 15,05 | 13,72 | 13,60 |
| (18) pyridinyl-4-ammoniumethyl phosphonate | a | 84 | $n_D^{25}$ = 1,5213 | 15,18 | 15,02 | 13,72 | 13,60 |
| (19) pyridinyl-3-ammoniumethyl phosphonate | a | 98,9 | $n_D^{25}$ = 1,5213 | 15,18 | 15,03 | 13,72 | 13,60 |
| (20) 3-picolyl-ammoniumethyl phosphonate | a | 93,0 | $n_D^{27}$ = 1,5130 | 14,20 | 14,03 | 12,83 | 12,34 |
| (21) thiazolinyl-2-ammoniumethyl phosphonate | a | 97,0 | $n_D^{25}$ = 1,5202 | 14,60 | 14,22 | 13,20 | 13,07 |
| (22) cyclopentyl-ammoniumethyl phosphonate | a | 91,7 | $n_D^{30}$ = 1,4622 | 15,87 | 15,69 | 7,17 | 7,19 |
| (23) 3,4-dichlorophenyl-ammoniumethyl phosphonate | a | 72,5 | 64–66° C. | 11,39 | 11,12 | 5,14 | 5,11 |
| | b | 52,8 | 66–67° C. | 11,39 | 11,07 | 5,14 | 5,11 |
| (24) 3'-(3,5-dichlorophenyl)-hydantoinethyl phosphonate | a | 62,0 | | | | | |
| (25) 2-benzimidazolyl-ammoniummethyl phosphonate | a | 95,0 | 155–160° C. | 12,74 | 12,25 | 17,27 | 16,90 |
| (26) 2-methoxy-ethyl-ammoniummethyl phosphonate | a | 84,5 | $n_D^{30}$ = 1,4425 | 16,73 | 16,38 | 7,56 | 7,42 |
| (27) 1,2,4-triazolyl-2-ammoniumethyl phosphonate | a | 89,6 | | 15,96 | 15,07 | 28,85· | 29,30 |
| (28) furfuryl-ammonium-octyl phosphonate | b | | | 10,64 | | 4,81 | |
| (29) furfuryl-ammonium-tridecyl phosphonate | b | | | | | | |
| (30) furfuryl-ammonium-isopropyl phosphonate | a | 95,4 | $n_D^{30}$ = 1,4648 | 14,01 | 14,27 | | |
| (31) furfuryl-ammonium-1-methoxy-2-propyl phosphonate | b | | | | | | |
| (32) furfuryl-ammonium-phenyl phosphonate | b | | | | | | |
| (33) 2-aminophenyl-ammoniumoctyl phosphonate | c | | | | | | |
| (34) 3-aminophenyl-ammoniumoctyl phosphonate | | | | | | | |
| (35) 3-nitro-2-aminophenyl-ammoniumoctyl phosphonate | | | | | | | |
| (36) 2,6-dichloro-4-aminophenyl-ammoniumoctyl phosphonate | | | | | | | |
| (37) 2,4-dimethyl-6-aminophenyl-ammoniumoctyl phosphonate | | | | | | | |
| (38) 3-aminopropyl-ammoniumethyl phosphonate | a | 95,5 | $n_D^{26}$ = 1,4688 | 16,82 | 16,70 | 15,20 | 14,90 |
| (39) 2-aminopropyl-ammonium-ethyl phosphonate | a | 95,1 | $n_D^{26}$ = 1,4642 | 16,82 | 16,90 | 15,20 | |
| (40) 6-aminohexyl-ammoniumethyl phosphonate | a | 98,9 | $n_D^{26}$ = 1,4678 | 13,69 | 13,11 | 12,38 | 12,10 |
| (41) 3-dimethyl-aminopropyl-ammonium-ethyl phosphonate | a | 94,6 | $n_D^{26}$ = 1,4536 | 14,60 | 14,78 | 13,19 | 12,90 |

TABLE I-continued

| Compound No. | Process variant | Yield (%) | Melting point $n_D$ | P (%) calculated | P (%) found | N (%) calculated | N (%) found |
|---|---|---|---|---|---|---|---|
| (42) nonyl-ammoniumethyl phosphonate | a | 97,5 | $n_D^{29} = 1,4430$ | 12,24 | 12,10 | 5,53 | |
| (43) tetradecyl-ammoniumethyl phosphonate | a | 99,8 | 45–46° C. | 9,58 | 10,12 | 4,33 | 4,50 |
| (44) hexadecyl-ammoniumethyl phosphonate | a | 97,0 | 50–52° C. | 8,82 | 8,92 | 3,98 | 4,10 |
| (45) octadecyl-ammoniumethyl phosphonate | a | 93,2 | 54–56° C. | 8,17 | 8,69 | 3,69 | 3,68 |
| (46) pentadecyl-ammoniumethyl phosphonate | a | 99,5 | 48–52° C. | 9,18 | 9,04 | 4,15 | 4,11 |
| (47) decyl-ammoniumethyl phosphonate | a | 98,7 | $n_D^{23} = 1,4472$ | 11,59 | 11,55 | 5,23 | 4,99 |
| (48) piperonyl-ammoniumethyl phosphonate | a | 97,6 | 57–59° C. | 11,87 | 11,60 | 5,36 | 5,26 |
| (49) bis(2-methoxyethyl)-ammoniumethyl phosphonate | a | 92,0 | $n_D^{25} = 1,4460$ | 12,74 | 12,73 | 5,76 | 5,86 |
| (50) cycloheptyl-ammoniumethyl phosphonate | a | 99,0 | $n_D^{23} = 1,4736$ | 13,86 | 13,81 | 6,27 | 6,20 |
| (51) 2-ethyl-1-hexyl-ammoniumethyl phosphonate | a | 98,3 | $n_D^{25} = 1,4472$ | 12,95 | 12,81 | 5,85 | 5,92 |
| (52) bis(2-ethylhexyl)-ammoniumethyl phosphonate | a | 89,2 | $n_D^{25} = 1,4530$ | 8,82 | 8,86 | 3,98 | 3,92 |
| (53) 4-aminophenyl-ammoniumethyl phosphonate | a | 94,0 | 190–194° C. | 14,21 | 14,00 | 12,84 | 12,80 |
| (54) 2-aminophenyl-ammoniumtridecyl phosphonate | b | 53,7 | 87–91° C. | 8,32 | 8,28 | 7,52 | 7,44 |
| (55) pyrimidinyl-2-ammoniummethyl phosphonate | a | 96,0 | | 15,10 | 14,90 | 20,48 | 20,30 |
| (56) 4-aminophenyl-ammoniumtridecyl phosphonate | c | | 98–102° C. | 8,32 | 8,22 | 7,52 | 7,20 |
| (57) hexamethylene-di-(ammoniumethyl phosphonate) | a | 96,3 | | 18,43 | 18,20 | 8,32 | 8,10 |
| (58) 1,2-propane-di-(ammoniumethyl-phosphonate) | a | 99,8 | $n_D^{30} = 1,4619$ | 21,06 | 20,90 | 9,52 | |
| (59) 1,3-propane-di-(ammoniumethyl phosphonate) | a | 98,9 | $n_D^{30} = 1,4655$ | 21,06 | 20,40 | 9,52 | |
| (60) N,N—diallyl-sec-butyl-ammoniumethyl phosphonate | a | 80,7 | | 11,77 | 12,06 | 5,31 | |
| (61) N,N—diallyl-ethyl-hexyl-ammoniumethyl phosphonate | a | 85,7 | | 9,70 | 9,20 | 4,38 | |
| (62) furfuryl-ammoniumethyl phosphonate | a | | | | | | |
| (63) 6-chloro-benzo-thiazolyl-2-ammoniumethyl phosphonate | a | 99,3 | | | | | |
| (64) 4-chloro-benzo-thiazolyl-2-ammoniumethyl phosphonate | a | | | | | | |
| (65) N,N—diallyl-ethanol-ammoniumethyl phosphonate | a | 98,7 | $n_D^{30} = 1,4726$ | 12,33 | 12,05 | 5,57 | |
| (66) tridecyl-ammoniumethyl phosphonate | a | 99,0 | 40–41° C. | 10,02 | 9,98 | 4,53 | 4,37 |
| (67) dodecyl-ammoniumethyl phosphonate | a | 95,0 | | 10,49 | 10,30 | 4,74 | 4,38 |
| (68) cyclopropyl-methane-ammoniumethyl phosphonate | a | 96,1 | $n_D^{27,5} = 1,4532$ | 17,11 | 17,07 | 7,73 | 7,60 |
| (69) 2-ethyl-1,3,4-thiadiazolyl-5-ammoniumethyl phosphonate | b | 98,0 | $n_D^{25} = 1,5031$ | 12,96 | 12,80 | 17,56 | 17,48 |
| (70) N—benzyl-isopropyl-ammoniumethyl phosphonate | a | 94,5 | $n_D^{23} = 1,5035$ | 11,95 | 11,87 | 5,40 | 5,67 |

TABLE I-continued

| Compound No. | Process variant | Yield (%) | Melting point $n_D$ | P (%) calculated | found | N (%) calculated | found |
|---|---|---|---|---|---|---|---|
| (71) dibenzyl-ammonium-ethyl phosphonate | a | 91,7 | 82–88° C. | 10,08 | 9,96 | 4,55 | 4,58 |
| (72) benzyl-ammoniume-thyl phosphonate | a | 95,7 | $n_D^{23} = 1,5145$ | 14,27 | 14,12 | 6,44 | 6,34 |
| (73) diphenyl-ammonium-ethyl phosphonate | a | 97,4 | 46–47° C. | 11,09 | 11,07 | 5,01 | 4,99 |
| (74) N—methyl-N,N—di-tri-decyl-ammoniumethyl phosphonate | a | 97,2 | $n_D^{27,5} = 1,4598$ | 6,13 | 6,05 | 2,77 | 2,85 |
| (75) N,N—dimethyl-2-ethyl-hexyl-ammoniumethyl phosphonate | a | 71,9 | $n_D^{27,5} = 1,4465$ | 11,59 | 11,40 | 5,24 | 5,20 |
| (76) di-tridecyl-ammonium-ethyl phosphonate | a | 96,7 | $n_D^{27,5} = 1,4585$ | 6,30 | 6,20 | 2,85 | 2,80 |
| (77) 3-stearyloxypropyl-ammoniumethyl phosphonate | a | 98,2 | 49–52° C. | 7,08 | 7,05 | 3,20 | 3,25 |
| (78) 3-tridecyloxypropyl-ammoniumethyl phosphonate | a | 98,9 | $n_D^{26,5} = 1,4555$ | 8,43 | 8,47 | 3,81 | 3,92 |
| (79) trihexyl-ammoniumethyl phosphonate | a | 99,5 | $n_D^{26,5} = 1,4505$ | 8,17 | 8,10 | 3,69 | 3,85 |
| (80) dihexyl-ammoniumethyl phosphonate | a | 99,5 | $n_D^{25} = 1,4450$ | 10,49 | 10,57 | 4,74 | 4,65 |

Further details of the invention are illustrated by the following non-limiting examples.

EXAMPLE 1

3-Isononyloxypropyl-ammoniummethyl phosphonate (compound of the formula I)

To a mixture of 11 g. (0.1 moles) of dimethyl phosphite, 20 ml. of water and 20 ml. of methanol a solution of 20.13 g (0.1 moles) of 3-isononyloxypropyl amine in 38 ml. of methanol is added dropwise, in 15 minutes, at room temperature. The reaction mixture is refluxed for 4 hours, whereupon the solvent and the ethylene formed are distilled off in vacuo. 28.2 g. of 3-isononyloxypropyl-ammoniummethyl phosphonate are obtained. Yield: 94.8%

Analysis:
calculated: C 52.49%, H 10.84%, N 4.71%, P 10.42%; found: C 52.29%, H 10.68%, N 4.57%, P10.30%.

According to thin layer chromatography the product is uniform and according to the IR spectrum the structure of the product corresponds to the assumed structure.

Typical IR bands are as follows:

| 2900 | (wide band) $\nu$ NH$_3^+$ | 1210 cm$^{-1}$ | $\nu$ P = O |
| 2320 | cm$^{-1}$ $\nu$ PH | 1115 | $\nu$ C—O—C |
| 1630 } | $\delta$ NH$_3^+$ | 990 | $\nu$ P—O |
| 1540 } | | | |
| 1460 } | $\delta$ CH$_2$, CH$_3$ | 770 | $\nu_s$ P—O—C |
| 1380 } | | | |
| 1365 } | | | |

EXAMPLE 2

3-Ethoxypropyl-ammoniummethyl phosphonate (compound of the formula (2))

A mixture of 11 g. (0.1 moles) of dimethyl phosphite, 20 ml. of water and 20 ml. of methanol is reacted with a mixture of 10.31 g. (0.1 moles) of 3-ethoxypropyl amine and 30 ml. of methanol as described in Example 1. 19.7 g. of 3-ethoxypropyl-ammoniummethyl phosphonate are obtained. Yield: 98.9%. $n_D^{30}$ 1.4425.

Analysis:
calculated: C 36.17%, H 9.10%, N 7.03%, P 15.56%; found: C 35.02%, H 9.05%, N 6.94%, P 19.37%.

According to thin layer chromatography the product is uniform.

EXAMPLE 3

3-Methoxypropyl-ammoniummethyl phosphonate (compound of the formula (3))

A mixture of 11 g. (0.1 moles) of dimethyl phosphite, 20 ml. of water and 20 ml. of ethanol is reacted with a mixture of 8.51 g. (0.1 moles) of 3-methoxypropyl amine and 30 ml. of methanol as described in Example 1. 18.5 g. of 3-methoxypropyl-ammoniummethyl phosphonate are obtained. Yield: 99.9%. $n_D^{30} = 1.4449$.

Analysis:
calculated: C 32.42%, H 8.70%, N 7.56%, P 16.73%; found: C 31.20%, H 8.63%, N 7.14%, P 16.45%.

According to thin layer chromatography the product is uniform. The IR spectrum corresponds to the assumed structure. Typical IR bands are as follows:

| 2900 | (wide band) $\nu$ NH$_3^+$ | 1210 cm$^{-1}$ | $\nu$ P = O |
| 2320 | cm$^{-1}$ $\nu$ PH | 1115 | $\nu$ C—O—C |
| 1630 } | $\delta$ NH$_3^+$ | 1055 | $\nu_{as}$ P—O—C |
| 1540 } | | 990 | $\nu$ P—O |
| 1460 } | $\delta$ CH$_2$, CH$_3$ | 770 | $\nu_s$ P—O—C |
| 1380 } | | | |
| 1365 } | | | |

EXAMPLE 4

3-Butyloxypropyl-ammoniummethyl phosphonate (compound of the formula (4))

A mixture of 11 g. (0.1 moles) of dimethyl phosphite, 20 ml. of water and 20 ml. of methanol is reacted with a mixture of 13.12 g. (0.1 moles) of 3-butyloxypropyl amine and 30 ml. of methanol as described in Example 1. 22.6 g. of 3-butyloxypropyl-ammoniummethyl phosphonate are obtained. Yield: 89.4%. $n_D^{30} = 1.4420$ Analysis:
calculated: C 42.27%, H 9.75%, N 6.16%, P 13.64%;
found: C 41.38%, H 9.54%, N 6.06%, P 13.63%.

According to thin layer chromatography the product is uniform. The IR spectrum corresponds to the assumed structure. Typical IR bands are as follows:

| 2900 | (wide band) ν NH$_3^+$ | 1210 cm$^{-1}$ | ν P = O |
|------|------|------|------|
| 2320 | cm$^{-1}$ ν PH | 1115 | ν C—O—C |
| 1630 } | δ NH$_3^+$ | 1055 | ν$_{as}$ P—O—C |
| 1540 } | | 990 | ν P—O |
| 1460 } | δ CH$_2$, CH$_3$ | 770 | ν$_s$ P—O—C |
| 1380 } | | | |
| 1365 } | | | |

EXAMPLE 5

3-Ethoxypropyl-ammoniummethyl phosphonate (compound of the formula (5))

A mixture of 13.81 g. (0.1 moles) of diethyl phosphite, 20 ml. of water and 20 ml. of ethanol is reacted with a mixture of 10.31 g. (0.1 moles) of 3-ethoxypropyl amine and 30 ml. of ethanol as described in Example 1. 21.3 g. (99.9%) of 3-ethoxypropyl-ammoniumethyl phosphonate are obtained.

Analysis:
calculated: C 39.42%, H 9.45%, N 6.56%, P 14.53%;
found: C 39.20%, H 9.30%, N 6.69%, P 14.05%.

According to thin layer chromatography the product is uniform.

EXAMPLE 6

3-Methoxypropyl-ammoniumethyl phosphonate (compound of the formula (6))

A mixture of 13.81 g. of diethyl phosphite, 20 ml. of water and 20 ml. of ethanol is reacted with a mixture of 8.91 g. (0.1 moles) of 3-methoxypropyl amine and 30 ml. of ethanol as described in Example 1. 18.8 g. of 3-methoxypropyl-ammoniumethyl phosphonate are obtained. Yield: 94.3%. $n_D^{30}$=1,4440

Analysis:
calculated: C 36.17%, H 9.10%, N 7.03%, P 15.56%;
found: C 35.97%, H 9.28%, N 7.17%, P 15.48%.

According to thin layer chromatography the product is uniform.

EXAMPLE 7

3-Isononyloxypropyl-ammoniumethyl phosphonate (compound of the formula (7))

A mixture of 13.81 g. (0.1 moles) of diethyl phosphite, 20 ml. of water and 20 ml. of ethanol is reacted with a mixture of 20.13 g. (0.1 moles) of 3-isononyloxypropyl amine and 30 ml. of ethanol as described in Example 1. $n_D^{30}$=1.4485 (liquid fraction).

Analysis:
calculated: C 53.99%, H 11.0%, N 4.49%, P 9.95%;
found: C 53.80%, H 10,97%, N 4,28%, P 9.73%.

According to thin layer chromatography the product is uniform.

EXAMPLE 8

3-Butyloxypropyl-ammoniumethyl phosphonate (compound of the formula (8))

A mixture of 13.81 g. (0.1 moles) of diethyl phosphite, 20 ml. of water and 20 ml. of ethanol is reacted with a mixture of 13.12 g. (0.1 moles) of 3-butyloxypropyl amine and 30 ml. of ethanol as described in Example 1. 23.1 g. of 3-butyloxypropyl-ammoniumethyl phosphonate are obtained. Yield: 95.7%. $n_D^{30}$=1.4438

Analysis:
calculated: C 44.79%, H 10.02%, N 5.80%, P 12.84%; found: C 43.87%, H 9.72%, N 5.27%, P 12.05%.

According to thin layer chromatography the product is uniform.

EXAMPLE 11

1-Methyl-2-phenoxy-ethyl-ammoniumethyl phosphonate (compound of the formula (11))

A mixture of b 13.81 g. (0.1 moles) of diethyl phosphite, 20 ml. of water and 20 ml. of ethanol is reacted with a mixture of 15.12 g. (0.1 moles) of 1-methyl-2-phenoxyethyl amine and 30 ml. of ethanol as described in Example 1. 21.4 g. of 1-methyl-2-phenoxyethyl-ammoniumethyl phosphonate is obtained. Yield: 81.9%. Melting point: 95°–96° C.

Analysis:
calculated: C 50.56%, H 7.71%, N 5.36%, P 11.86%;
found: C 50.09%, H 7.69%, N 5.29%, P 11.27%.

EXAMPLE 12

3,4-Dichlorophenyl-ammoniumethyl phosphonate (compound of the formula (23))

12.0 g. (0.05 moles) of 3,4-dichloroaniline hydrobromide and 21.0 g. (0.15 moles) of diethyl phosphite in 50 ml. of toluene are reacted at 108° C. The ethyl bromide formed is distilled off. After distillation of the solvent and the excess of diethyl phosphite in vacuo a thick, oily residue is obtained, which crystallizes upon addition of ether. 72.5 g. of 3,4-dichlorophenyl-ammoniumethyl phosphonate are obtained. Melting at 64° to 66° C.

Analysis:
calculated: C 35.31%, H 4.44%, P 11.39%, Cl 26.02%, N 5.14%; found: C 35.09%, H 4.08%, P 11.12%, Cl 25.97%, N 5.11%.

According to thin layer chromatography the product is uniform.

EXAMPLE 16

Tetradecyl-ammoniumethyl phosphonate (compound of the formula (43))

To a mixture of 34.6 g. (0.25 moles) of diethyl phosphite, 50 ml. of water and 50 ml. of ethanol a mixture of 53.4 g. (0.25 moles) of tetradecylamine and 70 ml. of ethanol is added. The reaction mixture is refluxed for 4 hours, whereupon the solvent is distilled off in vacuo. 80.7 g (99.8%) of tetradecyl-ammoniumethyl phosphanate are obtained, melting at 45° to 46° C.

Analysis:
calculated: P 9.58%, N 4.33%; found: P 10.12%, N 4.50%.

According to thin layer chromatography the product is uniform.

EXAMPLE 17

Hexadecyl-ammoniumethyl phosphonate (compound of the formula (44))

To a mixture of 34.6 g. (0.25 moles) of diethyl phosphite, 50 ml. of water and 50 ml. of ethanol 60.4 g (0.25 moles) of hexadecyl amine and 70 ml. of ethanol are added. The reaction mixture is refluxed for 4 hours, whereupon the solvent is distilled off in vacuo. 85.2 g.

of hexadecyl-ammoniumethyl phosphonate are obtained. Yield: 97.0%. Melting point: 50° 1 to 52° C.

Analysis:

calculated: P 8.82%, N 3.98%; found: P 8.92%, N 4.10%.

According to thin layer chromatography the product is uniform.

EXAMPLE 18

Octadecyl-ammoniumethyl phosphonate (compound of the formula (45))

To a mixture of 34.6 g. (0.25 moles) of diethyl phosphite, 50 ml. of water and 50 ml. of ethanol a mixture of 67.4 g. (0.25 moles) of octadecyl amine and 70 ml. of ethanol is added. The reaction mixture is refluxed for 4 hours, whereupon the solvent is distilled off in vacuo. 88.5 g. (93.2%) of octadecyl-ammoniumethyl phosphonate are obtained, melting at 54° to 56° C.

Analysis:

calculated: P 8.17%, N 3.69%.

According to thin layer chromatography the product is uniform.

The fungicidally active compounds of the general formula I can be employed within a wide range, depending on the fungi to be treated, on the climatic conditions etc. The treatment is generally performed with solutions containing 0.01 to 10 g. of active ingredient per liter of the solution.

Prior to use the compounds of the general formula I are converted into fungicidal composition, which comprise carriers and optionally surfactants in addition to the active ingredients.

As carriers organic or mineral, natural or synthetic materials can be used. The carriers promote the adsorption of the active compounds on the plants or on the soil and/or make the transport or handling of the compositions easier. Typical solid carriers include clays, natural and synthetic silicates, resins, waxes and solid fertilizers, etc. Typical liquid carriers are water, alcohols, ketones, mineral oil fractions, chlorinated hydrocarbons and condensed gases.

As surface active agents ionic or nonionic emulsifying, dispersin or wetting agents can be used. Suitable surfactants include polyacrylic acid salts and ligninexsulfonic acid salts, and the condensates of ethylene oxide with fatty alcohols, fatty acids and fatty amines.

The compounds of the general formula I and the above additives can be formulated for example as wettable powders, soluble powders, powder sprays, granulates, solutions, emulsifiable concentrates, emulsions, suspended concentrates and aerosols.

Typical powder sprays according to the invention have the following composition:

active ingredient 5–95%
wetting agent 0.2–3%
dispersing agent 2–10%
further additives 0–92.8%

The composition optionally may contain one or more stabilizing agents and/or further additives, e.g. absorption and adhesion promoting agents, anti-clotting agents.

A typical wettable powder according to the invention has the following composition:

active ingredient 50%
calcium-lignine sulfate (dispersing agent) 5%
anionic wetting agent (sodium-isopropyl-naphthalene sulfonate) 1%
silica (anti-clotting agent) 5%
kaoline (filling agent) 39%.

Water-soluble powders can for example be prepared by admixing 20 to 95% by weight of active ingredient with 0 to 10% by weight of an anti-clotting agent. The formulation may further include a water-soluble filling agent, preferably a salt. A typical water-soluble powder has the following composition:

active ingredient 70%
anionic wetting agent (sodium-isopropyl-naphthalene sulfonate) 0.5%
anti-clotting agent (silica) 5%
soluble filling agent (sodium sulphate) 24.5%

A typical wettable powder may have the following composition:

active ingredient 90%
Ethoxylated alcohols having 10 to 16 carbon atoms (wetting agent) 1%
calcium-ligninesulfonate (dispersing agent) 3%
inert filler 6%

According to the invention the compounds of the general formula I may be converted into aqueos dispersions and emulsions as well. Dispersions and emulsions are preferably prepared from wettable powders or emulsifiable concentrated by dilution with water. Water-in-oil and oil-in-water type emulsions can equally be prepared and their consistency is generally thick mayonnaise-like.

The compositions according to the invention optionally contain also further additives, e.g. protecting colloids, sticking and thickening agents, tixotrop agents and stabilizing agents.

The formulation of the compounds of the general formula I into plant protecting compositions is illustrated by the following examples.

EXAMPLE 20

Powder spray containing 3-methoxypropyl-ammoniumethyl phosphonate (compound of the formula (6)) as active ingredient 45% of active ingredient, 49% of Ultra-sil We-3 (silicate), 3% of Dispergiermittel SI (anionactive tenside and carrier) and 3% of Tensiofix LX spec. are thoroughly admixed and ground in a mill. A well floatable powder spray is obtained.

EXAMPLE 21

Powder spray containing 3-butoxypropyl-ammoniumethyl phosphonate (compound of the formula (8)) as active ingredient 45% of active ingredient, 49% of Ultra-sil VN 3, 3% of Dispergiermittel SI and 3% of Tensiofix LX spec. are thoroughly admixed and ground in a mill.

EXAMPLE 22

Emulsifiable concentrate containing 3-isononyloxypropyl-ammoniummethyl phosphonate (compound of the formula (1)) as active ingredient 75% of active ingredient and 25% of Emulsogen NO 90 are thoroughly admixed.

EXAMPLE 23

Emulsifiable concentrate containing tetradecyl-ammoniumethyl phosphonate as active ingredient (compound of the formula (43))

10% of active ingredient, 20% of Emulsogen NO 60 (alkyl-arylpolyglycol ether) and 70% of toluene are thoroughly admixed.

EXAMPLE 24

Emulsifiable spray mixture containing octadecyl-ammoniumethyl phosphanate as active ingredient (compound of the formula (45))

10% of active ingredient, 20% of Atlox 4857 B (a mixture of anionactive and non-ionic tenside) and 70% of monochlorobenzene are thoroughly admixed.

EXAMPLE 25

Emulsifiable spray mixture containing bis-(2-ethylhexyl)-ammoniumethyl phosphonate as active ingredient (compound of the formula (52))

40% of active ingredient, 10% of Emulsogen WO 6 and 50% of Isoforon are thoroughly admixed.

The fungicidal activity of the compound according to the invention was tested on Botrytis Cinerea and Fusarium oxysporum fungi by "partially poisoned agar plate" method.

According to this method to suspensions or solutions containing the active compounds to be tested in various concentrations the spore suspensions of the test fungi are added in a 1:1 volume ratio. The obtained combination contains the active ingredient in the desired concentration. For example if the fungicidally active compound is to be tested in a concentration of 1600 ppm, to 1 ml. of a solution containing 3200 ppm of said fungicide 1 ml. of spore suspension is added.

A potato-dextrose culture medium was prepared in a conventional way. After cooling to 60° C. 40-ml. portions of the culture medium were admixed with the solutions of the test compounds as described above. The solutions obtained were poured into Petri dishes having a diameter of 10 cm.

Of one-week old cultures of Botrytis Cinerea and Fusarium oxysporum discs having a diameter of 5 mm. were cut out. Four discs were placed into each Petri dish. The Petri dishes were incubated at 25° C. for 6 days. Evaluation was carried out by measuring the diameters of the colonies at the time when in the control dishes the colonies almost reached each other. The tests were carried out in four repetitions. The results obtained are given in the following Tables II and III.

TABLE II

Result of "poisoned agar plate tests" carried out on *Botrytis Cinerea* fungi

| Test compounds | Diameter of colony (mm) in the case of different concentration of active test compounds | | | |
|---|---|---|---|---|
| | 1600 ppm | 800 ppm | 400 ppm | 100 ppm |
| METAXANIN | | | | |
| 0,1-N—(2,6-dimethylphenyl)-N—(2'-methoxyacetyl)-alanine-methylester | 16.6 | 16.6 | 16.8 | 17.2 |
| EFOSITE-AL | | | | |
| Aluminium-tris-ethyl-phosphonate | m | m | 11.5 | 14.3 |
| compound of formula (1) | 0 | 0 | 0 | 1.5 |
| compound of formula (2) | 11.5 | 11.7 | 11.7 | 12.7 |
| compound of formula (3) | 11.3 | 11.3 | 11.5 | 12.5 |
| compound of formula (4) | m | m | 2.7 | 5.3 |
| compound of formula (5) | m | m | m | 2.1 |
| compound of formula (6) | 0 | 0 | 0 | 0 |
| compound of formula (7) | 0 | 0 | 0 | 0 |
| compound of formula (8) | m | m | m | m |
| compound of formula (9) | 5.6 | 9.0 | 9.0 | 12.3 |
| compound of formula (10) | m | m | 8.7 | 10.5 |
| compound of formula (11) | 0 | 9.3 | 9.7 | 10.5 |
| compound of formula (12) | 5.3 | 5.8 | 5.8 | 10.2 |
| compound of formula (13) | m | m | 8.7 | 8.9 |
| compound of formula (14) | m | m | 10.2 | 12.3 |
| compound of formula (15) | m | 8.7 | 8.9 | 10.5 |
| compound of formula (16) | 8.7 | 9.2 | 10.5 | 13.2 |
| compound of formula (17) | 5.8 | 8.5 | 8.7 | 8.9 |
| compound of formula (18) | 10.2 | 10.7 | 10.7 | 10.7 |
| compound of formula (22) | m | m | m | m |
| compound of formula (25) | m | 6.5 | 7.2 | 8.5 |
| compound of formula (26) | m | m | 2.7 | 8.5 |
| compound of formula (42) | m | 6.5 | 6.7 | 8.5 |
| compound of formula (46) | m | 2.3 | 3.5 | 4.2 |
| compound of formula (47) | m | 2.0 | 2.5 | 3.7 |
| compound of formula (48) | m | 6.5 | 6.7 | 8.2 |
| compound of formula (49) | m | 5.3 | 6.5 | 7.8 |
| compound of formula (50) | m | 3 | 3.5 | 4 |
| compound of formula (54) | m | m | 3.0 | 5.1 |
| compound of formula (55) | 0 | 0 | 0 | 2.7 |
| compound of formula (62) | 2 | 5.2 | 5.7 | 6.5 |
| compound of formula (66) | 0 | 0 | m | 1.5 |
| compound of formula (67) | 0 | 0 | m | 1.5 |
| compound of formula (70) | 0 | m | m | 1.7 |

Untreated control 16.5
m - growth started but stopped after a very short time

TABLE III

Results of "poisoned agar plate tests" carried out on *Fusarium oxysporum* fungi

| Test compounds | Diameter of colony (mm) in the case of the different concentration of active test compounds | | | |
|---|---|---|---|---|
| | 1600 ppm | 800 ppm | 400 ppm | 100 ppm |
| METAXANIN | | | | |
| 0,1-N—(2,6-dimethylphenyl)-N—2'-methoxy-acetyl)-alanine-methylester | 16.6 | 16.5 | 17.4 | 21.2 |
| EFOSITE-AL | | | | |
| Aluminium-tris-ethyl-phosphonate | 12.5 | 12.5 | 13.0 | 18.5 |
| compound of formula (1) | 0 | 0 | 0 | 0 |
| compound of formula (2) | 14.6 | 14.6 | 15.8 | 15.8 |
| compound of formula (3) | 13.9 | 13.8 | 15.3 | 15.3 |
| compound of formula (4) | m | m | m | m |
| compound of formula (5) | m | m | m | m |
| compound of formula (6) | m | m | m | m |
| compound of formula (7) | 0 | 0 | m | m |
| compound of formula (8) | m | m | m | m |
| compound of formula (10) | m | m | m | m |
| compound of formula (19) | 10.2 | 10.2 | 12.5 | 12.5 |
| compound of formula (20) | 8.7 | 9.2 | 9.8 | 10.2 |
| compound of formula (21) | 5.3 | 5.8 | 6.2 | 7.8 |
| compound of formula (22) | m | m | m | m |
| compound of formula (23) | m | m | 5.7 | 8.2 |
| compound of formula (24) | 5.7 | 8.2 | 9.4 | 12.1 |
| compound of formula (25) | 3.5 | 4.2 | 5.2 | 5.4 |
| compound of formula (26) | m | m | 2.7 | 8.8 |
| compound of formula (27) | m | 5.2 | 5.7 | 9.8 |
| compound of formula (28) | 5.7 | 8.5 | 8.5 | 8.7 |
| compound of formula (29) | 5.3 | 7.5 | 8.7 | 8.5 |
| compound of formula (30) | 5.5 | 6.7 | 7.7 | 9.5 |
| compound of formula (31) | 5.8 | 8.7 | 9.1 | 9.1 |
| compound of formula (32) | 4.5 | 5.2 | 6.2 | 6.2 |
| compound of formula (33) | 10.5 | 10.7 | 10.7 | 11.2 |
| compound of formula (34) | 2.9 | 5.7 | 8.5 | 8.5 |
| compound of formula (35) | 4.2 | 4.8 | 5.2 | 6.7 |
| compound of formula (36) | 4.5 | 5.7 | 6.8 | 7.1 |
| compound of formula (38) | 5.7 | 6.1 | 6.1 | 7.2 |
| compound of formula (39) | 5.0 | 6.1 | 6.7 | 6.9 |
| compound of formula (40) | 2.1 | 3.5 | 3.7 | 4.1 |
| compound of formula (41) | 3.2 | 3.5 | 3.7 | 3.7 |
| compound of formula (42) | 1.5 | 3.0 | 3.6 | 4.2 |
| compound of formula (43) | 3.0 | 5.2 | 5.8 | 5.9 |
| compound of formula (44) | 5.0 | 5.7 | 6.2 | 7.5 |
| compound of formula (45) | 6.1 | 6.7 | 6.9 | 7.3 |
| compound of formula (46) | 2.9 | 3.5 | 3.9 | 4.5 |
| compound of formula (47) | m | 2.2 | 3.5 | 4.1 |
| compound of formula (50) | m | 3.0 | 3.5 | 4.1 |
| compound of formula (51) | 5.1 | 6.5 | 6.7 | 8.2 |
| compound of formula (55) | 5.6 | 6.7 | 7.8 | 8.0 |
| compound of formula (53) | 5.7 | 6.5 | 6.9 | 7.1 |
| compound of formula (52) | 0 | 0 | 0 | 5.7 |
| compound of formula (56) | 2.3 | 2.7 | 3.1 | 3.5 |
| compound of formula (57) | 5.5 | 6.7 | 8.3 | 8.5 |
| compound of formula (58) | 3.5 | 3.7 | 3.9 | 4.5 |
| compound of formula (59) | 3.7 | 3.9 | 5.7 | 5.9 |
| compound of formula (60) | 2.7 | 4.8 | 4.9 | 4.9 |
| compound of formula (61) | 2.6 | 3.1 | 3.5 | 4.5 |
| compound of formula (62) | 2 | 2.7 | 2.9 | 5.7 |
| compound of formula (63) | 0 | 0 | 5.2 | 6.5 |
| compound of formula (64) | 2.7 | 3.8 | 4.2 | 5.3 |
| compound of formula (65) | m | m | 2.5 | 3.7 |
| compound of formula (66) | 0 | m | m | 2.7 |
| compound of formula (67) | 0 | m | m | m |
| compound of formula (68) | 0 | m | 1.5 | 3.2 |
| compound of formula (69) | 2.7 | 3.8 | 4.2 | 4.7 |
| compound of formula (70) | m | m | 2.8 | 6.5 |
| compound of formula (71) | 2.5 | 4.1 | 5.0 | 5.7 |
| compound of formula (72) | 2.8 | 5.6 | 4.2 | 4.8 |
| compound of formula (73) | 2.0 | 4.1 | 4.5 | 5.1 |
| compound of formula (74) | 2.0 | 2.5 | 3.5 | 3.7 |
| compound of formula (75) | 3.5 | 4.2 | 5.3 | 8.1 |
| compound of formula (76) | 3.7 | 4.1 | 4.7 | 5.2 |
| compound of formula (77) | 2.5 | 8.1 | 8.7 | 8.8 |
| compound of formula (78) | 4.5 | 5.7 | 8.2 | 10.5 |
| compound of formula (79) | 2.3 | 4.1 | 4.5 | 5.7 |
| compound of formula (80) | 2.5 | 2.8 | 2.9 | 10.1 |

Untreated control 12.5
m - growth started but stopped after a very short time

The biologiccal test results unambiguously show that the compounds according to the invention exhibit fungicidal activity which generally surpasses the fungicidal activity of known structurally related compounds.

PHYTOPHTORA INFESTANS TEST

Leaf-discs of a diameter of 15 to 18 mm of apical and 2–3 leaves of tomato seedlings having 4–6 leaves grown in green-house were abscrised. The leaf-discs were placed on a filter paper and the leaves were treated on their surface with the fungicide and after drying the abaxial surface of the leaves was treated with the spray.

A double filter paper disc was placed into the bottom of Petri-dishes and a slide of a microscope was put on it in cross-form, and it was sterilized at 100° C.

After cooling the filter paper was wet with sterile distilled water. The leaf discs were placed on the slide and the suspension of the pathogen was sprayed on the leaf-discs.

The Petri dishes were incubated at 10° C. for 48 hours and then at 20°–22° C. until the symptoms occurred.

The evaluation was performed on the 4th day after the treatment.

The results were evaluated as follows:
0 no infection
1 infected surface 1–30%
2 infected surface 31–60%
3 infected surface 61–90%
4 infected surface 91–100%.

TABLE IV

Test results - *Phytophtora infestans*

| Active ingredient | Evaluation in case of different active ingredient concentrations | | | |
|---|---|---|---|---|
| | 2000 ppm | 1000 ppm | 500 ppm | 100 ppm |
| compound of formula (1) | 0 | 0 | 0.4 | 1.0 |
| compound of formula (7) | 0 | 0.4 | 0.4 | 1.4 |
| compound of formula (8) | 1.6 | 2.0 | 3.2 | 3.2 |
| compound of formula (20) | 0 | 0 | 1 | 2 |
| compound of formula (21) | 0 | 0 | 0.4 | 0.8 |
| compound of formula (60) | 0 | 0 | 0.4 | 1 |

TABLE IV-continued

Test results - *Phytophtora infestans*

| Active ingredient | Evaluation in case of different active ingredient concentrations | | | |
|---|---|---|---|---|
| | 2000 ppm | 1000 ppm | 500 ppm | 100 ppm |
| compound of formula (67) | 0 | 0 | 0.4 | 1 |
| compound of formula (52) | 0 | 0 | 0 | 0.7 |
| METAXANIN | | | | |
| 0.1-N—(2,6-dimethyl-phenyl)-N (2'-methoxy-acetyl)-alanine-methylester | 0.6 | 1 | 1 | 1.2 |
| EFOSITE-AL | | | | |
| Aluminium-tris-ethyl-phosphonate | 1.2 | 1.2 | 2.6 | 2.6 |
| Infected control | 4 | | | |

We claim:
1. Phosphoric acid monoester salts having the formula I

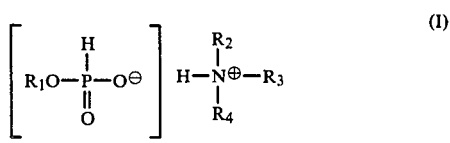

wherein
$R_1$ is a straight or branched chain alkyl having 1 to 13 carbon atoms;
$R_2$ is alkoxyalkyl with 1 to 16 carbon atom in the alkoxy portion and 1 to 4 carbon atoms in the alkyl portion, alkenyl having 2 to 4 carbon atoms, alkinyl having 2 to 4 carbon atoms, aminoalkyl wherein the alkyl portion has from 1 to 6 carbon atoms, alkylaminoalkyl wherein the alkyl portions have 1 to 4 carbon atoms, alkylphosphonate ammoniumalkyl wherein the alkylphosphonate portion has 1 to 4 carbon atoms in the alkyl portion and the remaining alkyl has 1 to 6 carbon atoms;
$R_3$ is hydrogen, alkenyl having 2 to 5 carbon atoms, and alkoxyalkyl wherein the alkoxy portion has 1 to 4 carbon atoms and the alkyl portion has 1 to 4 carbon atoms;
$R_4$ is hydrogen.

* * * * *